Aug. 26, 1975 J. NOWALK Plant Pat. 3 773
AZALEA PLANT
Filed Sept. 16, 1974
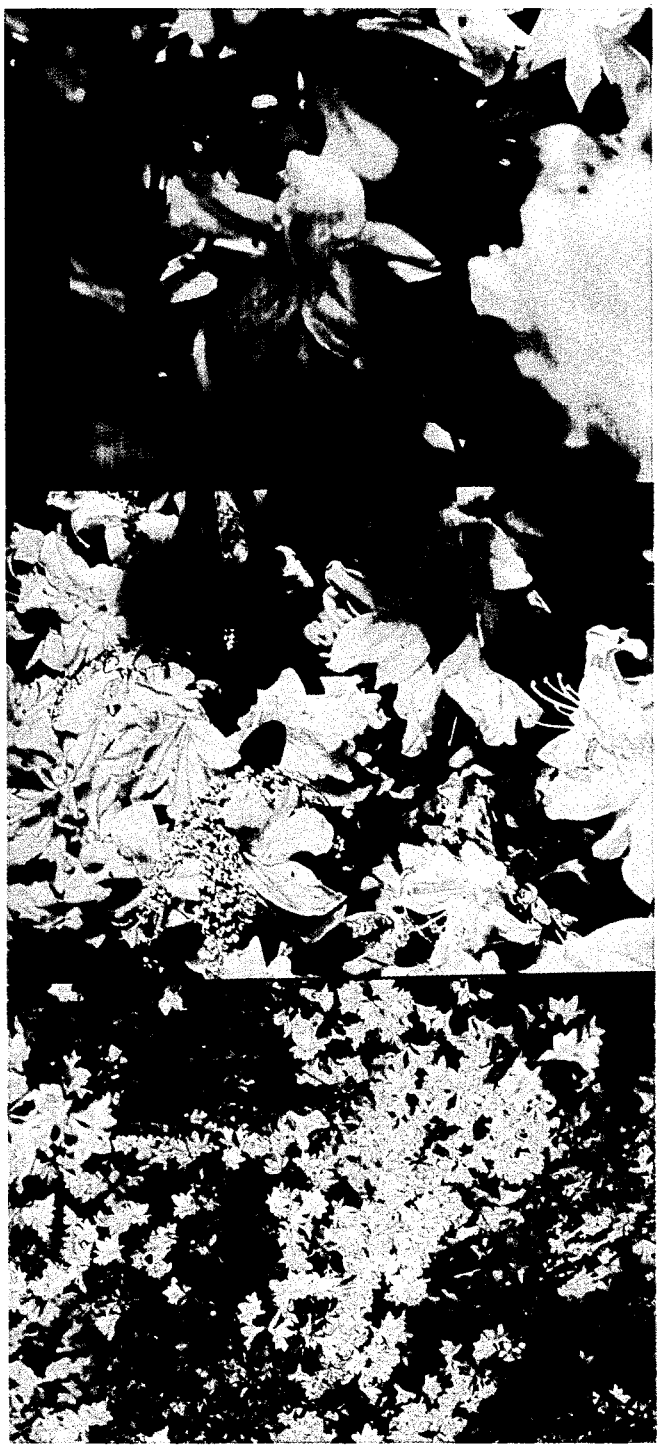

United States Patent

Plant Pat. 3,773

Patented Aug. 26, 1975

3,773

AZALEA PLANT

Joseph Nowalk, R.D. 3, Box 404A, Amwell Road, Somerset, N.J. 08873

Filed Sept. 16, 1974, Ser. No. 506,607

Int. Cl. A01h 5/00

U.S. Cl. Plt.—56 1 Claim

The present invention relates to a new and distinct variety of azalea plant which was discovered by me as a cultivated sport of the azalea variety known as "Crimson Hinodegiri" (unpatented).

At the time of my discovery, I was growing a number of "Crimson Hinodegiri" plants in my home garden located in Somerset, N.J. During one winter season, one of these plants was severely winter-blasted, but in the following spring, I cut it back to a single four-inch stump to see if it was completely dead. After several weeks, much to my surprise, I noticed new shoots growing out of the stump, so I carefully preserved the shoots and kept them under close observation. In due course, I found that the original plant had apparently sported, and the sport growth formed a vigorous and compact plant which bore attractive foliage of light olive green color slightly lighter than the normal foliage color of the parent variety "Crimson Hinodegiri." The following year, the sport bloomed, and instead of the normal red blooms of single form that are characteristic of the parent variety, the flowers of the sport were a deep rose pink in color and were hose-in-hose in form.

Continued observations of the original sport, as well as progeny thereof which were propagated by me by cuttings and grown in my garden aforesaid, revealed other distinctive features and have convinced me that the sport is definitely a new and distinct variety of azalea plant which is distinguished from its parent variety, as well as from all other azalea varieties of which I am aware, as evidenced by the following unique combination of principal characteristics which are outstanding therein and are established and transmissible through succeeding propagations:

(1) A vigorous and compact habit of growth;
(2) Attractive light olive green foliage which is slightly lighter in color than the foliage of the parent variety "Crimson Hinodegiri";
(3) Abundant flowers which entirely cover the plant when it is in full bloom;
(4) A very attractive hose-in-hose flower form and deep rose pink flower color;
(5) An unusual habit of the terminal leaves in remaining vertical and completely enclosing the flower buds and initially giving the impression that the plant bears no flower buds at all, until about 2 weeks before coming into bloom, when the terminal leaves fold down to a horizontal position to expose the flowers;
(6) Very good hardiness, with the ability to withstand temperatures as low as −20° F. without injury;
(7) Excellent suitability for Easter season greenhouse forcing and even in very hot weather without wilting; and
(8) Very good resistance to fungus, lace bugs, chlorosis and other diseases without the need for spraying.

The accompanying drawing shows typical specimen plants of my new azalea variety, as well as views on a larger scale of typical flowers borne thereon, as depicted in color as nearly true as it is reasonably possible to make the same in a color illustration of this character.

The following is a detailed description of the new variety, with color terminology in accordance with the Exotic Horticultural Color Guide, published by Roehrs Company, of Rutherford, N.J., except where general color terms of ordinary dictionary significance are obvious:

LOCALITY WHERE GROWN AND OBSERVED: Somerset, N.J.

PARENTAGE: Sport of "Crimson Hinodegiri."

PROPAGATION: Holds its distinguishing characteristics through succeeding propagations by cuttings.

PLANT:
- Form—Bushy; upright.
- Habit—Vigorous; compact.
- Rooting—Coordinate; roots easily.
- Blooming habit—Profuse; flowers cover entire plant.
- Blooming season—Usually second and third weeks of May outdoors in New Jersey.
- Suitability for forcing—Excellent, particularly for Easter season and even during very hot weather without wilting.

FOLIAGE:
- Size—Medium.
- Quantity—Abundant.
- Color — New foliage—Upper side—Light olive green; under side—Pale green. Old foliage—Upper side—Dark green; under side—slightly lighter green than upper side.
- Shape—Oval.
- Texture—Upper side—Glossy; smooth. Under side—Semi-glossy; smooth.
- Margin—Smooth and clean-cut.
- Disease resistance—Excellent resistance to fungus, lace bug, chlorosis and other diseases to which azalea plants are normally subject, without any need of spraying, as determined by comparison with other azalea varieties grown in close proximity and under the same conditions which had to be frequently sprayed for such diseases in my garden in Somerset, N.J.

FLOWERS:
- Borne—In clusters; on stems of medium length.
- Size—Average about 1¾ inches.
- Quantity of bloom—Abundant, both outdoors and in greenhouse.
- Continuity—Continuous; blooms usually last at least one week longer than those of "Crimson Hinodegiri."
- Permanence—Very strong persistence.
- Petalage—Number of petals under normal conditions—Usually 10.
- Color—Deep Rose Pink, ranging from near Rose Pink, Color No. 37 to near Rose, Color No. 38 (Exotica).
- Texture—Soft.
- Appearance—Star-shaped.
- Form—Hose-in-hose.

BUD:
- Size—Length—About ½ inch. Width—About ¼ inch.

HARDINESS: Excellent; has withstood below zero weather as low as −20° F. without injury in Somerset, N.J.

I claim:

1. A new and distinct variety of azalea plant, substantially as herein shown and described, characterized particularly as to novelty by the unique combination of a vigorous and compact habit of growth, attractive light olive geen foliage which is slightly lighter in color than the foliage of the parent variety "Crimson Hinodegiri," abundant flowers which entirely cover the plant when it is in full bloom, a very attractive hose-in-hose flower form and deep rose pink flower color, an unusual habit of the terminal leaves in remaining vertical and completely enclosing the flower buds and initially giving the impression that the plant bears no flower buds at all, until about 2 weeks before coming into bloom, when the terminal leaves fold down to a horizontal position to expose the flowers, very good hardiness, with the ability to withstand temperatures as low as −20° F. without injury, excellent suitability for Easter season greenhouse forcing and even in very hot weather without wilting, and very good resistance to fungus, lace bugs, chlorosis and other diseases without the need for spraying.

No references cited.

ROBERT E. BAGWILL, Primary Examiner